United States Patent [19]

Scott et al.

[11] Patent Number: 5,030,008
[45] Date of Patent: Jul. 9, 1991

[54] METHOD AND APPARATUS FOR THE AUTOMATED ANALYSIS OF THREE-DIMENSIONAL OBJECTS

[75] Inventors: Richard S. F. Scott, Woodside, Calif.; Yoram Uziel, Yodfat, Israel; Franco A. Filice, Gilroy, Calif.

[73] Assignee: KLA Instruments, Corporation, San Jose, Calif.

[21] Appl. No.: 255,212

[22] Filed: Oct. 11, 1988

[51] Int. Cl.$^5$ ............................................. G01B 11/24
[52] U.S. Cl. ................................... 356/394; 356/376; 356/237; 358/101; 358/106; 382/8
[58] Field of Search ............... 356/237, 372, 373, 375, 356/376, 394; 358/101, 106; 382/8

[56] References Cited

U.S. PATENT DOCUMENTS

| | | | |
|---|---|---|---|
| 4,648,053 | 3/1987 | Fridge | 382/8 X |
| 4,677,473 | 6/1987 | Okamoto et al. | 382/8 X |
| 4,876,455 | 10/1989 | Sanderson et al. | 356/376 X |

FOREIGN PATENT DOCUMENTS

| | | | |
|---|---|---|---|
| 2741807 | 3/1979 | Fed. Rep. of Germany | 356/376 |
| 2185813 | 7/1987 | United Kingdom | 356/237 |

Primary Examiner—F. L. Evans
Attorney, Agent, or Firm—Rosenblum, Parish & Bacigalupi

[57] ABSTRACT

An optomechanical system for illuminating and imaging selected portions of a three dimensional object having specularly reflective surfaces, including a two dimensional image sensor for receiving light reflected from the selected portions and producing an analog output signal representing a two dimensional image of the selected portions over a predetermined time period, a video digitizer for receiving and converting the analog output signal to a digital signal, and an image computer for receiving the digital signal output by the video digitizer, comparing the information obtained from the output digital signal to the stored specifications of a master of the imaged portion of the object, indicating whether the imaged object meets the specifications of the master, controlling the movement of the imaged object, and controlling the operation of the system.

31 Claims, 8 Drawing Sheets

| | LEAD FRAME OFF-SET | DIE OFF-SET | BALL BONDS | CRESENT BONDS | X-Y BONDING WIRE-PATH | BONDING WIRE HEIGHT |
|---|---|---|---|---|---|---|
| ILLUMINATION — BOTTOM | O | | | | | |
| ILLUMINATION — NARROW ANGLE | | O | O | O | | |
| ILLUMINATION — SLIGHT ANGLE | | | | O | O | O |
| ILLUMINATION — WIDE ANGLE | | | | | O | O |
| MAGNIFICATION — LOW | O | O | O | | | |
| MAGNIFICATION — HIGH | | | | O | | |
| APERTURE SETTINGS — TELECENTRIC SLIDE | IN | IN | IN | IN | IN | OUT |
| APERTURE SETTINGS — FIELD STOP | OUT | OUT | OUT | IN | OUT | OUT |

FIG. 10

METHOD AND APPARATUS FOR THE AUTOMATED ANALYSIS OF THREE-DIMENSIONAL OBJECTS

BACKGROUND OF THE INVENTION

1. Field of the Invention

The present invention relates generally to optical analysis systems, and more particularly, to an automated optical inspection system capable of making a three-dimensional analysis of an object, and even more specifically, an automated optical analysis system for inspecting the integrity and quality of electrical lead connections (wire bonds) between the pads of an integrated circuit and the conductive fingers of a lead frame prior to encapsulation.

2. Brief Description of the Prior Art

Because of their extremely small physical size, integrated circuit (IC) devices are normally packaged in an assembly which includes a protective housing for the IC and a plurality of conductive strips which facilitate connection of the IC to other electrical and electronic devices.

More specifically, during the packaging operation, the IC dies are attached to a lead frame which consists of an elongated strip of metal which has been etched to form a plurality of arrays of elongated conductors. Each array generally has one conductor with a central area (the lead frame island) upon which one die rests, and which acts as a grounding plane or heat sink for the die, and a number of connection fingers. After the die is placed on the island of the lead frame, the electrodes or pads of the die are connected to corresponding fingers of the lead frame plate by extremely thin bonding wires. Automatic wire bonders are capable of creating an interconnection of fine wire between an electrode of the die and a finger of the lead frame plate in 250 microseconds or less. See Dreibelbis et al, U.S. Pat. No. 4,586,642, issued May 6, 1986.

Although the production of integrated circuits is highly automated, trained human inspectors are still typically utilized to analyze the integrity and quality of the wire bonds before encapsulation. The process of inspecting the quality and integrity of the bonds and bonding wires placed by the wire bonders on the lead frame assemblies is commonly referred to as "bond inspection."

Because humans have relatively short attention spans and are prone to health related problems when employed for inspecting minute objects, the human inspectors have proven to be too unreliable for such exacting work. The high volume of integrated circuit manufacture, the high cost of human labor, and the unreliability of human inspectors has also typically resulted in unsatisfactory quality yields for semiconductor products. At the present time, bond inspection is merely a statistical quality control device rather than an accurate method for detecting bonding failures prior to encapsulation of the assembly.

The inability to detect bonding failures prior to encapsulation can result in significant increases in the cost of producing integrated circuits. Automated bond inspection systems, which would eliminate the human error inherent in the present bond inspection process, have been created which are capable of making two dimensional optical measurements of the electrical connections of the semiconductor assembly. However, because the measurements are only in two dimensions, the prior art systems have been unable to determine the placement and size of bonds, as well as the path or height of the bonding wires.

Methods of maximizing the gradient of an imaged object to bring the object into focus and thereby determine the distance from the imaging system to the object are well known. In an article by Gerd Hausler and Eva Korner, "Imaging with Expanded Depth of Focus," *Zeiss Information*, Oberkochen, 29, 9–13 (1986-/87), No. 98E, it is suggested that by increasing the depth of focus of the imaging system by taking a number of different images of the same object at different heights from the object and then recombining those images, a single image of greatly improved clarity can be produced. However, even this improved quality two-dimensional image does not reduce the noise associated with the maximized gradient to a point that such a method can be practically utilized in a number of applications where a high optical contrast is required between the imaged object and its background.

A three dimensional bond inspection system has been developed by View Engineering, Inc., of Chatsworth, Calif. This system uses a number of different video cameras and standard illuminations to create three dimensional images of the assembly and its connections by correlating images taken from different optical points of view. A significant problem associated with using a standard illumination technique in bond inspection and other applications is that the background, in this case the lead frame leads, fingers and pads, and the object being analyzed, the wires, ball bonds or crescent bonds, are quite often made from similar materials and reflect relatively equal quantities of light. Thus, although a three dimensional inspection system may be able to make three dimensional comparisons of the assembly, the poor contrast between the desired object and the undesired background makes such systems of limited usefulness. In addition, multi-camera systems which image and illuminate from a variety of different optical points of view can be as slow, unreliable and costly as human inspectors, thereby providing semiconductor manufactures with little incentive to automate the bond inspection process.

In Sanderson, Weiss, and Nayar's article, "Structured Highlight Inspection of Specular Surfaces," *IEEE Transactions on Pattern Analysis and Machine Intelligence*, Vol. 10, No. 1, January 1988, a method is suggested for illuminating and imaging specular surfaces of a three-dimensional object which will yield information regarding the surface height of the object and its orientation. Two approaches are suggested by this article, a single optical perspective structured highlight approach and a stereo structured highlight approach. Both approaches use one or more fixed imaging devices and a multiple of different light sources, each illuminating the object at different angles of incidence, to recreate a three-dimensional object in two-dimensions. However, because both systems require multiple images of the same portion of the object from different illumination perspectives, a significant amount of time and computation is required to create the desired imaging information.

SUMMARY OF THE PRESENT INVENTION

List of Objectives of the Invention

In view of the foregoing, it is therefore a primary objective of the present invention to provide a novel automated analysis system for determining the physical characteristics of selected portions of three dimensional objects having specularly reflective surfaces.

Another object of the present invention is to provide a novel automated bond inspection system capable of effectively analyzing the quality and integrity of the electrical connections between a semiconductor and lead frame connection assembly in three dimensions from a single optical point of view.

Another object of the present invention is to provide a novel automated bond inspection system capable of making a three dimensional determination of the size and shape of bonds between a semiconductor and lead frame connection assembly.

Another object of the present invention is to provide a novel automated bond inspection system capable of making an accurate three dimensional determination of the height of bonding wires between a semiconductor and lead frame connection assembly with respect to either the lead frame island, the die, or the lead frame support.

A further object of the present invention is to provide a novel automated bond inspection system capable of making a two dimensional determination of the distance between adjacent bonding wires between a semiconductor and lead frame connection assembly.

A still further object of the present invention is to provide a novel method for inspecting the bonds between a semiconductor and lead frame connection assembly utilizing an automated bond inspection system capable of effectively making a three dimensional analysis of the integrity and quality of the bonds from a single optical point of view.

A still further object of the present invention is to provide a novel method for inspecting the bonds between a semiconductor and lead frame connection assembly by illuminating and imaging the lead frame so as to increase the optical contrast between the imaged object and the background of that object.

An additional object of the present invention is to provide a method for determining the alignment of a die on a lead frame, the quality of the ball and crescent bonds of wires connecting the die to the lead frame, the path and separation between the wires connecting the die and the lead frame, and the height of those wires.

List of Advantages of the Invention

An important advantage of the present invention is that the automated bond inspection system is capable of making a three dimensional analysis of the bonding wires and bonds between the semiconductor and lead frame connection assembly without being hampered by poor optical contrast problems, and requiring only a single optical point of view.

Brief Description of the Preferred Embodiment

Briefly, a preferred embodiment of the automated bond inspection system of the present invention includes an optomechanical system for illuminating and imaging the bonding wires and electrical connections between a semiconductor and lead frame connection assembly to a two dimensional image sensor which produces an analog output signal representing a two dimensional image of the object over a predetermined time period, a video digitizer for receiving and converting the analog output signal to a digital signal, and an image computer for receiving the digital signal output by the video digitizer, comparing the information obtained from the output digital signal to the stored specifications of a master of the imaged portion of the assembly, indicating whether the imaged assembly meets the specifications of the master, controlling the movement of the imaged assembly, and controlling the operation of the optomechanical system.

These and other objects and advantages of the present invention will no doubt become apparent to those skilled in the art after having read the following detailed description of the preferred embodiment which is contained in and illustrated by the various drawing figures.

DESCRIPTION OF THE PREFERRED EMBODIMENT

Figure 1:
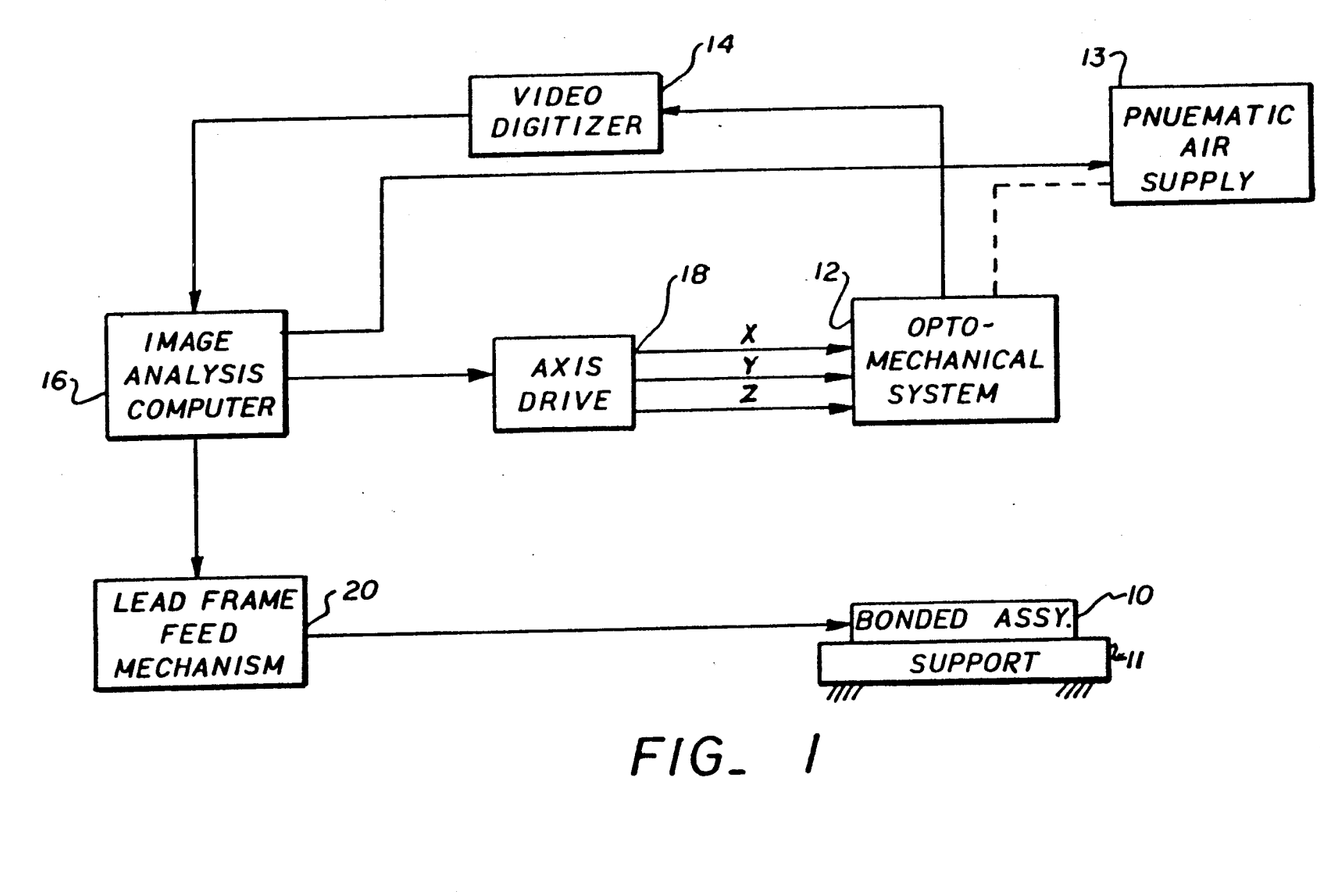
FIG. 1 is a diagram schematically illustrating an automated semiconductor to lead frame connection assembly inspection system in accordance with a preferred embodiment of the present invention.

With reference now to FIG. 1, an automated bond inspection system in accordance with the preferred embodiment of the present invention is schematically illustrated. A wire bonded semiconductor and lead frame assembly 10 is placed upon an electrically grounded supporting carrier or substrate 11 for inspection. These assemblies are typically produced in mass quantities on lead frame strips so that the finished assemblies may be sequentially inspected by simply pulling the strip past the bond inspection system. The supporting carrier 11 is equipped to support and control the positioning of the assemblies during their inspection.

The optomechanical system 12 illuminates and images the assembly 10 with a complex illumination and imaging system which effectively captures the three dimensional characteristics of the imaged assembly 10 from a single optical point of view and develops video signals corresponding thereto. The illumination and imaging of system 12 is partially controlled through pneumatically powered instruments within system 12. Pressurized air for the pneumatic instruments is supplied by pneumatic air supply 13. A video signal digitizer 14 receives the analog output representation of the assembly 10 from system 12 and converts it to a digital signal for input to image analysis computer 16.

Computer 16 receives the signals from the digitizer 14 and analyzes the digital information representing the imaged portion of the assembly 10 to determine if any manufacturing defects in the bonding of the die and lead frame have occurred. Prior to inspecting assemblies for a particular semiconductor type, a training operation can be performed which sets the specifications for that type of assembly in the memory of the computer 16. Detected signals from the imaged objects are then compared to the master reference created during the training operation. Assemblies coming within the specifications of the master assembly pass the inspection.

Typical manufacturing problems which can cause an inspected assembly to be rejected by the system include bonds which have been misplaced on either the die or the lead frame fingers, bonding wires which have broken, adjacent bonding wires which either touch or are too close to one another, poor quality bonds, bonding wires which are too close to the lead frame island, and bonding wires which are too long or too high. In addition to analyzing the imaged assembly 10, the computer 16 operates to control the movement of the system 12, air supply 13, axis drive 18 and the lead frame feed mechanism 20. Drive 18 controls the positioning of system 12 along the X, Y, and Z-axes. Mechanism 20 controls the positioning of the strip of bonded assemblies to be inspected by the system.

Figure 2:
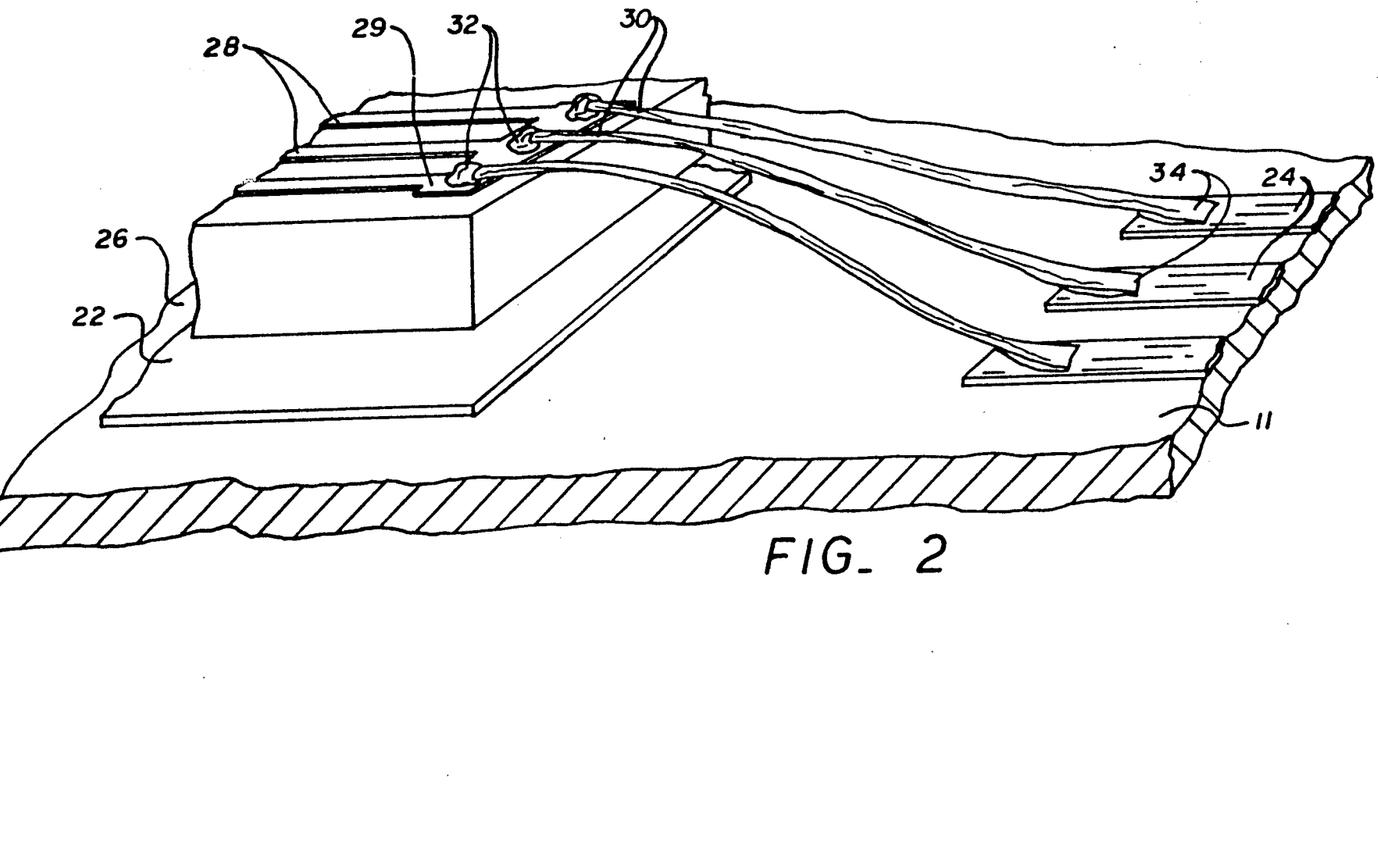
FIG. 2 is a partially cutaway, perspective view of a semiconductor to lead frame connection assembly prior to encapsulation.

A portion of a bonding area of a semiconductor to lead frame connection assembly 10 is illustrated in the partially broken, perspective view depicted in FIG. 2. The lead frame described above is shown comprised of island 22 and leads or connection fingers 24, and is depicted as resting upon a support carrier 11. Island 22 creates a mechanical support and heat sink or electrical ground for the semiconductor device or die 26. Metal traces 28 connected to the circuitry portion (not shown) of die 26 run to the edges of die 26 and form bonding pads or electrodes 29. Bonding wires 30 provide an electrical connection between the fingers 24 and bonding pads 29. Where the automated wire bonder has attached a bonding wire 30 to a bonding pad 29 by sonic bonding, a ball bond 32 is created. Where the automated wire bonder has attached a bonding wire 30 to a finger 24 by sonic bonding, a crescent bond 34 is created.

Optomechanical system 12 is capable of illuminating and imaging the desired object in a number of manners, the purpose of which will be further illustrated below. System 12 may be moved in the X, Y and Z-axes directions by drive 18 so that the entire assembly 10 may be imaged either in whole or in part. Typically, a large portion of the bonded assembly 10 is imaged at one time, such that only a small number of images are required to completely image each bonded assembly.

Figure 3:
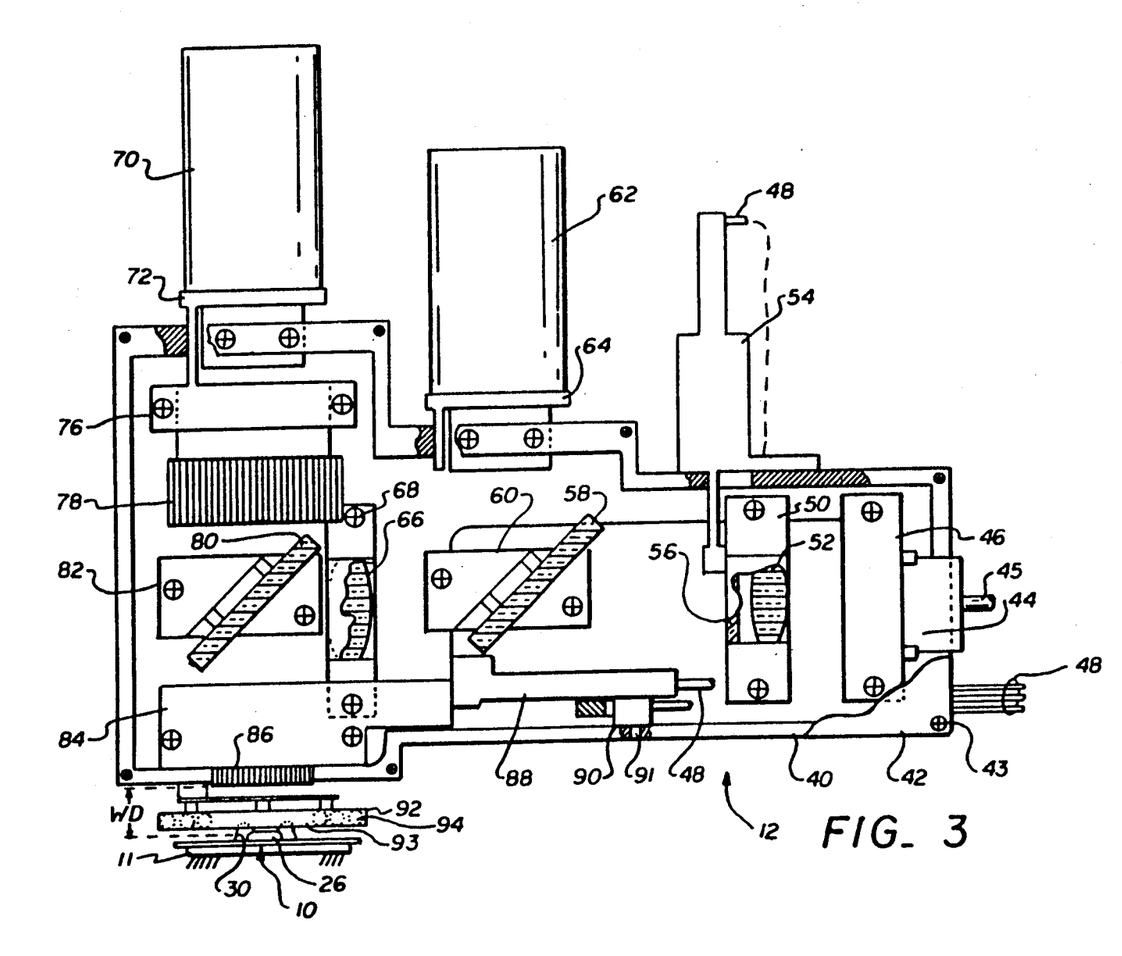
FIG. 3 is a perspective, partial cross-sectional view of an optomechanical system in accordance with the preferred embodiment of the present invention.

Referring now to FIG. 3, an embodiment of an optomechanical system in accordance with the present invention is depicted in partially broken section at 12. Note that system 12 is disposed immediately above the support 11 (containing a light source not shown) and wire bonded assembly 10, which includes a lead frame to which semiconductor die 26 is attached. The pads 29 of die 26 are electrically connected to the fingers 24 of the lead frame by wires 30, as is more clearly illustrated in FIG. 2. An optics case or housing 40 encloses most of the optomechanical components of system 12. A cover plate 42, attached with screws 43 to case 40, is depicted as cutaway to expose the internal components of the system 12.

One means of illuminating the assembly 10 is provided by a bright field illuminator 44, which casts a narrow angle beam of light rays (collimated or parallel light rays) onto assembly 10. The illuminator 44 is utilized in a number of imaging applications, particularly when a bright field of illumination of the background is required to create a proper optical contrast between the background and the desired object. Narrow angle light rays are typically generated by a xenon strobe flash unit (not shown) external to the system 12 which is connected to illuminator 44 through fiber optic cable 45. The diameter of the fiber optic cable 45 must be large enough to fill the desired optical aperture of illumination.

Light emitted by bright field illuminator 44 passes through a condenser lens 52 which is attached to case 40 by a holder 50. Lens 52 is an aspheric lens, the surface of which has been modified slightly from a spherical surface in order to reduce optical aberrations caused by the greater distance that the narrow angle light rays must travel to reach the bonded assembly 10. Condenser lens 52 preferably has a focal length of 25 mm, although this specification can change depending on the application and the size of the optomechanical system 12. A pneumatically activated field stop assembly 54, associated with holder 50, is utilized to position a field stop aperture 56 in or out of the beam path of illuminator 44. Pressurized air for the pneumatic control of the field stop assembly 54 and various other pneumatic instruments of optomechanical assembly 12 is supplied through a bundle of pneumatic tubing 48. Aperture 56 is primarily used in conjunction with high magnification camera 62 to limit the illumination field of view, as will be further described below.

Light rays from illuminator 44 then pass through a beam splitter 58, held in place by a holder 60, and into an achromatic lens assembly 66. Assembly 66 is a compound lens combination which has the same focal length for at least two different wavelengths and serves to insure that narrow angle light is directed to the bonded assembly 10 Lens assembly 66 is attached to the optics case 40 by a holder 68.

Light rays passing through lens assembly 66 are reflected downwardly by a beam splitter 80 through the aperture of a telecentric slide stop assembly 84. The telecentric assembly 84 is basically a telescopic system having an aperture stop at the image side of an object lens 86. The assembly 84 is telecentric on the image side of the lens 86.

The aperture stop of telecentric assembly 84 is also equipped with an array of selectively actuable light emitting diodes for use in some illumination applications. The telecentric assembly 84 is moved in and out of alignment with the optical axis under the control of a pneumatic actuator 88. An air diffuser assembly 90 is also provided, and attached to optics case 40 by a screw 91, to maintain a positive air pressure within optics case 40, thereby preventing dust and debris from entering optics case 40.

Light rays either passing through telecentric slide stop assembly 84, or generated therefrom, are directed to the object to be imaged by a lens 86, which is a standard lens (such as a closed-circuit television lens) having a focal length of approximately 25 mm, although this can depend upon the application for the lens. Lens 86 directs light collected from an object at a working distance, WD, which is the distance from the object side of lens 86 to the point of interest on or above the bonded assembly 10. Since the object within the working distance WD is in the focal plane of the object lens 86, the light rays after the object lens are collimated.

A circular dark field illuminator 92, having a central aperture 93 with a diameter somewhat larger than the area of the object to be imaged, is positioned beneath the lens 86 and above the die 26 to illuminate the various surfaces of the bonded assembly at a shallow or wide angle. Light emitting diodes, or LED's 94, provide selectively actuable light sources for illuminator 92 as will be further discussed below.

Regardless of the source of the illumination cast upon the bonded assembly 10, i.e. from bright field illuminator 44, telecentric slide stop assembly 84, or dark field illuminator 92, some light will normally be reflected from the assembly 10 and be collected and directed by lens 86 into both a high magnification camera 62 via the reflective surfaces of splitters 89 and 58 and a low magnification camera 70 after passage through splitter 80. Camera 62 is secured to case 40 by a bracket 64. Although light is directed to both cameras 62 and 70, images are only selectively digitized depending on the application. In applications utilizing the low magnification camera 70, imaged light is directly transmitted through splitter 80 and an imaging lens 78 to camera 70 where an image is then digitized. Imaging lens 78, in this application, preferably has a focal length of 35 mm, and is secured to case 40 by a holder 76. Camera 70 is secured to case 40 by a bracket 72. Each camera is equipped with image sensors comprised of rows and columns of light detectors which develop signals corresponding to each pixel of the illuminated object.

Optomechanical system 12 operates on a three dimensional coordinate system. The X-axis of the system is parallel to the length of the lead frame strip and the Y-axis is directed transverse to the length of the lead frame strip. The Z-axis of the coordinate system is perpendicular to the upper surface of the lead frame strip and coincides with the optical axis of system 12. The origin of coordinate system X, Y and Z is at the forward focal point of the lens 86. Images reflected to cameras 62 and 70 are recorded in a two dimensional X'Y'coordinate system which is in the plane of the image sensors of cameras 62 and 70.

Figures 4, 5, 6A, 6B, 6C:
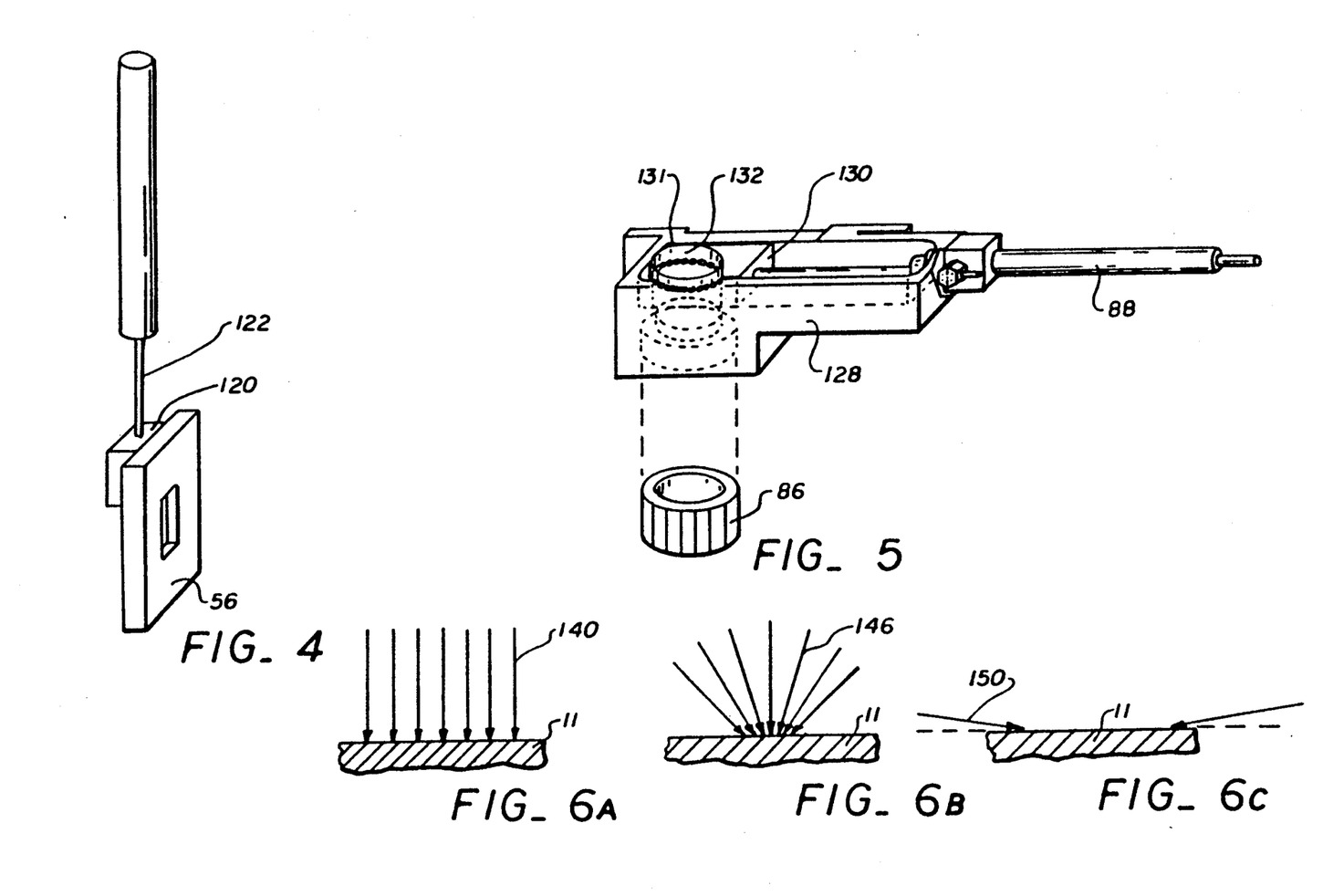
FIG. 4 is a perspective view of a field stop in accordance with the preferred embodiment of the present invention.
FIG. 5 is a partially exploded, perspective view of a telecentric slide assembly in accordance with the preferred embodiment of the present invention.
FIGS. 6a, 6b and 6c are pictorial illustrations of various illumination patterns which may produced by an optomechanical assembly in accordance with the preferred embodiment of the present invention.

Field stop assembly 54 may be better understood through reference to FIG. 4. Assembly 54 is comprised of a field stop aperture 56, a support bracket 120 and a pneumatic actuator 122. When high magnification camera 62 is to be utilized, aperture 56 is positioned in line with the optical axis of light transmitted by illuminator 44 so as to limit light projected onto the object to the field of view of camera 62.

A partially exploded, perspective view of telecentric slide stop assembly 84 is depicted in FIG. 5. The assembly 84 is comprised of a base 128 which is fixed relative to case 40 (FIG. 3), a slide 130 having an aperture 131 formed therein, and an LED ring 132 disposed around the perimeter of aperture 131. The slide 130, which supports LED ring 132, is positioned "in" and "out" of alignment with the optical axis of system 12 by the pneumatically controlled actuator 88. When the slide 130 is "out" of alignment with the optical axis of system 12, the numerical aperture of telecentric slide stop assembly 84 is approximately 0.36. When the slide 130 is "in" alignment with the optical axis of optomechanical assembly 12, the numerical aperture of telecentric slide stop assembly 84 is approximately 0.1. When it is desired to have a broad field of illumination, but a narrow field of imaging, one or more of the light sources is activated and slide 130 is moved "in." If the same illumination but a wider field of imaging is desired, slide 130 can be moved "out." The numerical aperture of slide 130 has no effect on the field of illumination. A broad field of illumination can be obtained at any angle of incidence, since the angle of incidence is not necessarily dependent upon the field of view.

FIGS. 6a, 6b and 6c illustrate the different modes, or angles of incidence of illumination that can be created by system 12 depending on the light source utilized. In FIG. 6a, illuminator 44 is the source of the narrow angled or collimated vertical light rays 140. In FIG. 6b, LED ring 132 is the source of the slight angled light rays 146. In FIG. 6c, LED's 94 are the source of the wide angled (or low angle to the support 11) light rays 150. Depending on the application, each type of illumination, either narrow angle, slight angle, or wide angle illumination, can be utilized independently or in some combination to create the desired illumination effect of the bonded assembly 10.

For example, fingers 24, pads 29, bonding wires 30, ball bonds 32 and crescent bonds 34 as depicted in FIG. 2, are all typically made from materials having similar surface reflectivity. This makes it difficult to distinguish light reflected from the various object surfaces on the basis of reflectivity alone. However, the objects of interest, such as the bonds and wires all have the common characteristics of having surfaces that are more or less rounded, while the background surface areas, such as the pads and lead frame fingers are generally flat.

If a rounded object is illuminated by light rays which have an angle of incidence as close to being parallel to the optical axis as possible, such as when illuminated by illuminator 44, and the telecentric slide 130 is "in" so that there is a small numerical aperture for imaging, only light rays reflected from the background surfaces and from the small portion of the rounded surface object which is perpendicular or nearly perpendicular to the optical axis will be collected by the camera. Thus, the camera will see the rounded object surfaces as primarily dark, except for a small area in the middle, while the flat background surfaces will appear light, or as a bright field.

Figure 7A:
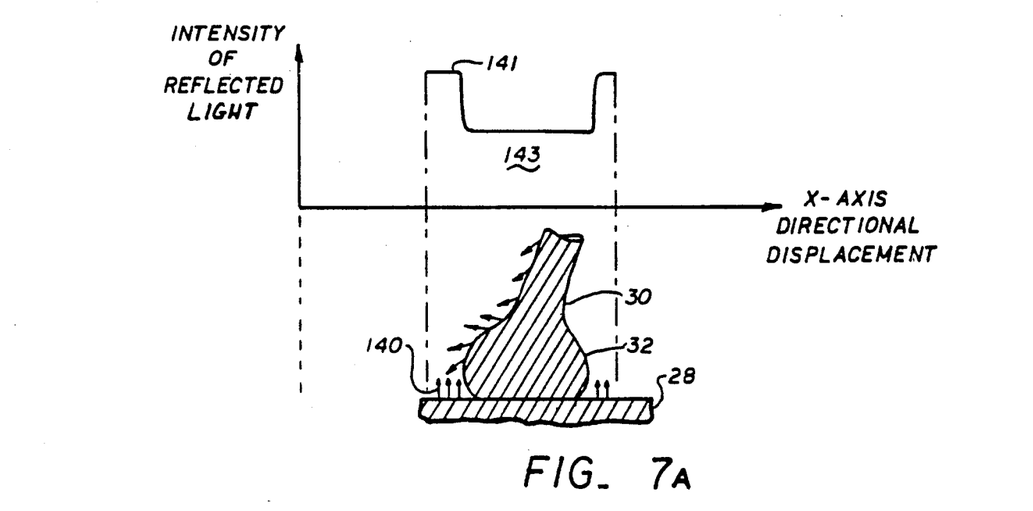
FIGS. 7a, 7b and 7c are cross-sectional representations of how collimated light rays are reflected by ball bonds, bonding wires, and crescent bonds, respectively, and graphic illustrations of the intensity of reflected light from the cross-sectioned objects as detected by the imaging cameras across the X-axis, respectively.

How the different illumination modes are utilized to analyze all of the different portions of the bonded assembly 10 can be better illustrated with reference to FIGS. 7a, 7b, and 7c. FIG. 7a depicts a cross-section representation of how collimated light rays 140 are reflected off the surface of a pad 29, a ball bond 32, and a connected bonding wire 30. The line graph located above the cross-section object represents the intensity of light reflected from the object as collected by the camera 62 or 70. The mostly flat surface of pad 29, which has a normal vector approximately parallel to the optical axis, reflects light directly back through object lens 86 to either camera 62 or 70 and as illustrated at 141 produces the highest intensity of reflected light detected by the image sensors of either imaging camera.

The line graph depicted in FIG. 7a illustrates that a unique graphic representation of an imaged object can be created using this technique. The electrical signal equivalent to this graphic representation can be used to determine certain physical characteristics of the ball bond 32 which can then be compared to specifications corresponding to a master of the same ball bond stored in the image analysis computer 16. As indicated at 143, the intensity of light reflected from rounded objects and detected by the camera is lower than the intensity of light reflected and detected from flatter object surfaces. Thus, the somewhat flattened portion of ball bond 32 reflects more light back to the imaging sensor at a higher intensity, and light reflected off of the edge of ball bond 32 is at a lower intensity. Hence, it is possible to produce sufficient information regarding an object from which certain measurements of the object can be taken from a single image of that object, rather than having to recreate an image of the object from a number of different images, either taken from different angles relative to the object or from a single optical point of view with illumination from a number of different angles of incidence.

Figure 7B:
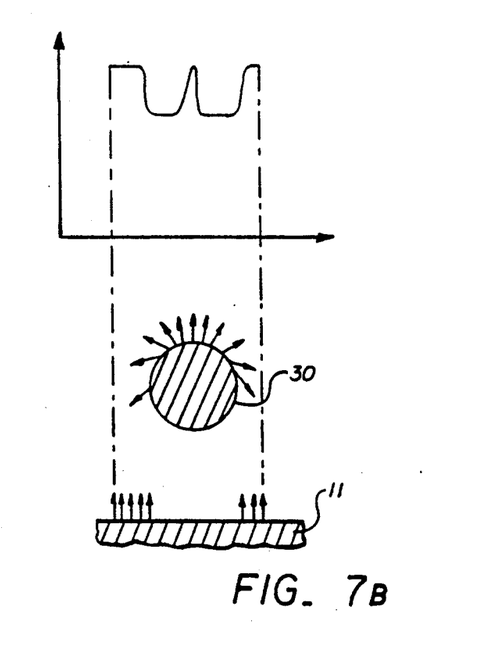
Figure 7C:
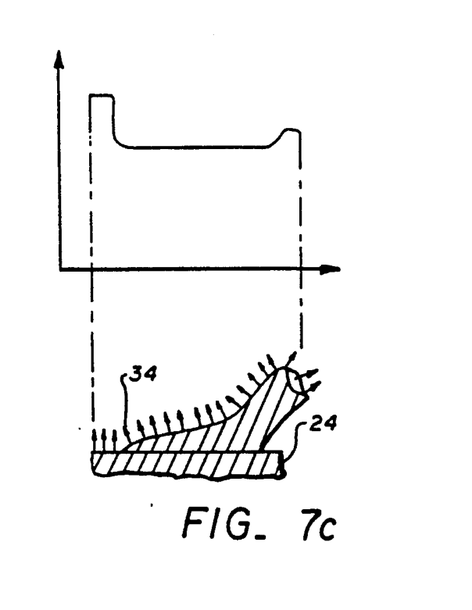

Similar unique graphic representations can be created for other aspects of the bonded assembly 10, such as is depicted in FIG. 7b for a bonding wire 30 and FIG. 7c for a crescent bond 34. Graphic representations may also be made for the intensity of light reflected from various other object surfaces versus Y-axis or Z-axis relative directional displacement. For instance, the intensity of reflected light versus Z-axis directional displacement can be utilized to determine the height of a bonding wire 30 with respect to any other surface of the bonded assembly 10, as will be further discussed below.

Figure 8A:
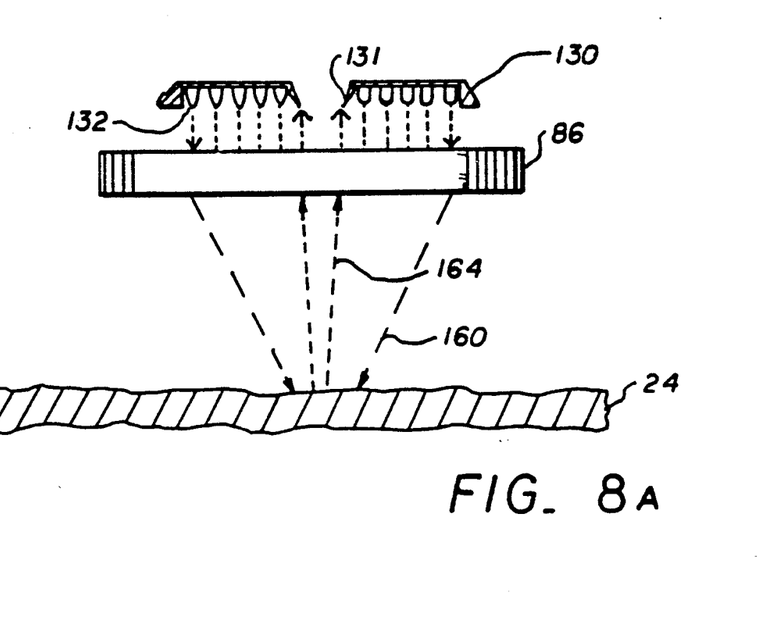
FIGS. 8a and 8b are pictorial illustrations of the illumination cones and imaging cones achievable through usage of a telecentric slide in accordance with the preferred embodiment of the present invention.

FIG. 8a further represents how, through usage of the telecentric slide stop assembly 84, the same optics can be utilized for various optical measurements. As depicted in part, slide 130 has been cut-away to reveal LED ring 132 which is used to control the illumination and imaging of the slightly irregular surface of lead fingers 24. LED ring 132 may be a single row of LED's disposed around the perimeter of aperture 131 as depicted in FIG. 5, or as a number of LED's located on the object side of the slide 130. In this later configuration, slide 130 and LED ring 132 are configured similarly to dark field illuminator 92 and its LED's 94.

As described above, moving the slide 130 "in" or "out" of coaxial alignment with the optical axis of system 12 can vary both the imaging and illuminating numeric apertures of the object lens 86. The numeric aperture is the quantity of n sin u, where n is the refractive index of the medium between the object and the lens, and u is the angular radius of the lens as seen from a point on the optical axis at the object. By varying the numeric aperture, the depth of field of the optics system can be changed, thereby making it possible to utilize a large imaging numeric aperture in some situations and a small imaging numeric aperture for other applications, while maintaining the same illuminating numeric aperture.

FIG. 8a illustrates that the angle of illumination or the illuminating numeric aperture can be selectively varied without affecting the imaging numeric aperture. The intensity of a point light source within the focal plane of the lens 86 will only be effected by light rays reflected from underlying or adjacent areas. If an adjacent or underlying area is illuminated by the illumination cone 160 in such a way as to direct reflected light rays away from the imaging cone 164 and the imaging camera, a desired object may be differentiated.

FIG. 8a also demonstrates how a small portion, rather than the entire illuminated area, of the total illuminated surface of crescent bond 34 can be imaged by an imaging camera. The surface of lead finger 24 is formed from a number of microscopic planes which are inclined at small angles to the optical axis of system 12. When this surface is illuminated and imaged through a small aperture, a speckled appearance will result because not all light rays reflected from the entire surface can be collected by the imaging camera. The speckled appearance may be eliminated by illuminating at a larger numerical aperture and imaging at a small numerical aperture, thereby preserving a large depth of focus and causing light from the surface of the lead finger 24 to also be collected by the imaging optics.

Figure 8B:
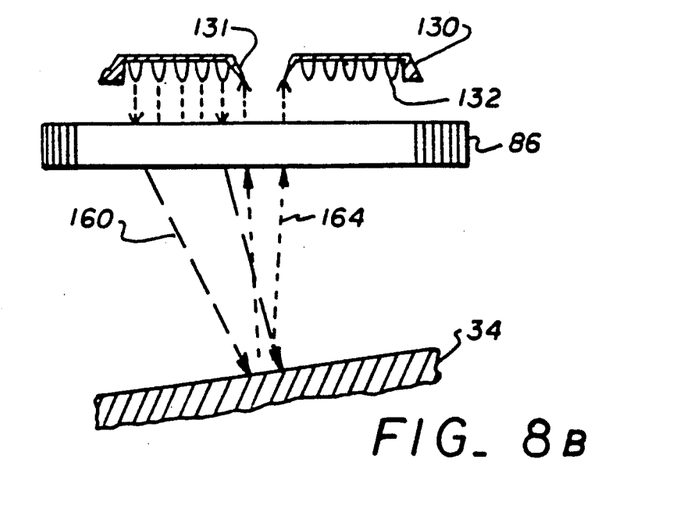

In addition, FIG. 8b further demonstrates that the illumination cone 160 need not be circularly symmetrical about the optical axis of system 12. As long as the approximate orientation of the surface of crescent bond 34 is known, that surface may be selectively illuminated to take advantage of surface variations. By selectively illuminating a portion of the LED's in LED ring 132, light rays reflected from the inclined surface of crescent bond 34 may be projected through aperture 131.

Alternatively, the angle of incident light may be selectively varied by backlighting a diffuse surface located in the focal plane of the lens 86 and controlling the light emission by an electrically controlled liquid crystal pattern.

By selectively varying the angle of incident illumination, the illuminating and imaging numeric apertures of system 12, and the position of system 12 and the bonded assembly 10, the entire bonded assembly 10 can be effectively imaged by system 12 and analyzed for compliance with its specifications by computer 16. However, before bonded assembly 10 can be analyzed, an optimum or best focus must be established for system 12 at each position over the bonded assembly. The best focus for system 12 is generally calculated through application of a Van Neumann architecture computer, which is utilized to determine the local maximum for normalized energy density at a selected point on the bonded assembly.

Figure 9A:
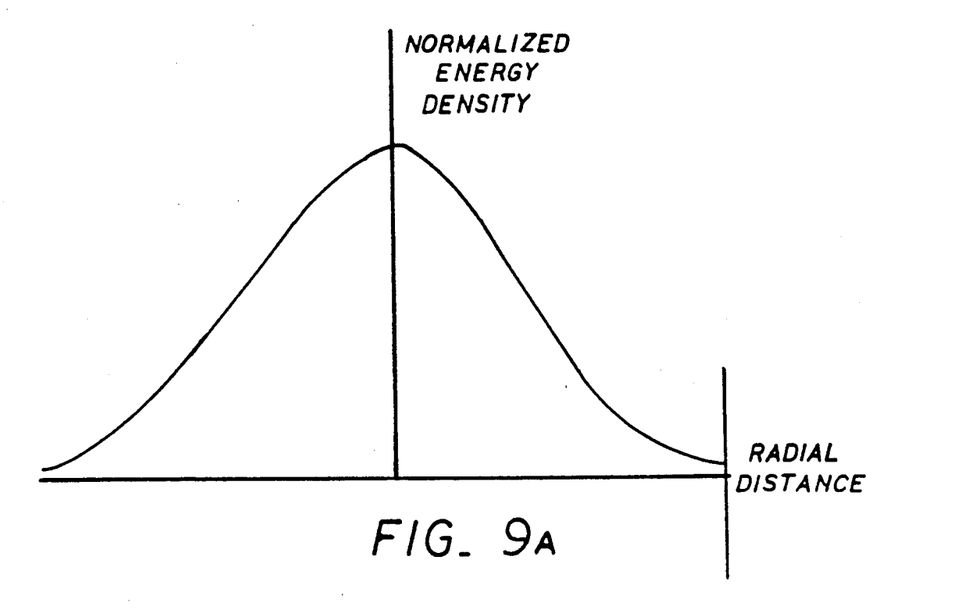
FIG. 9a is a graphic representation of the point spread function for an imaged object by an in-focus system.
Figure 9B:
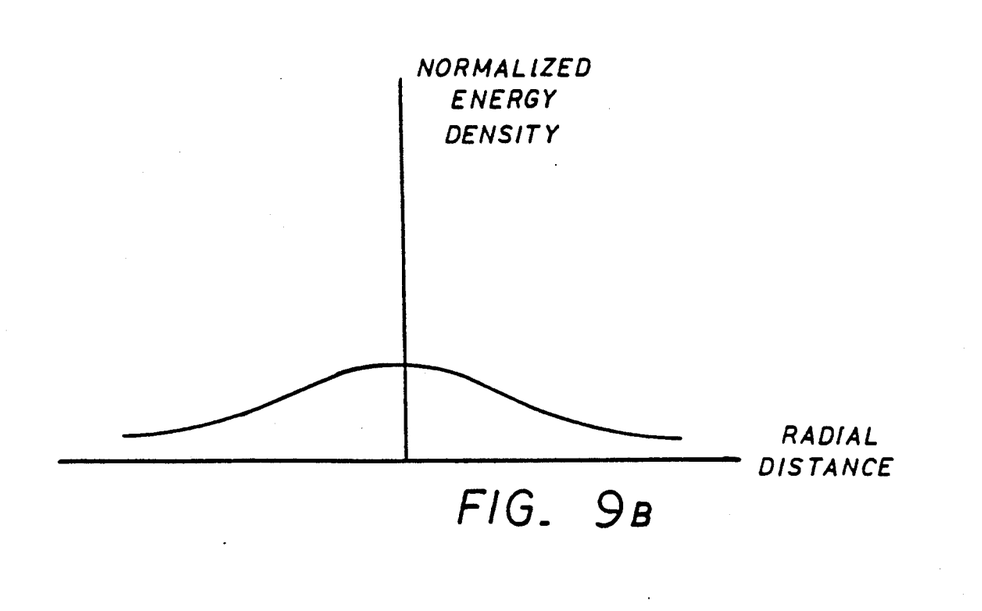
FIG. 9b is a graphic representation of the point spread function for an imaged object by an out-of-focus system.
Figure 10:
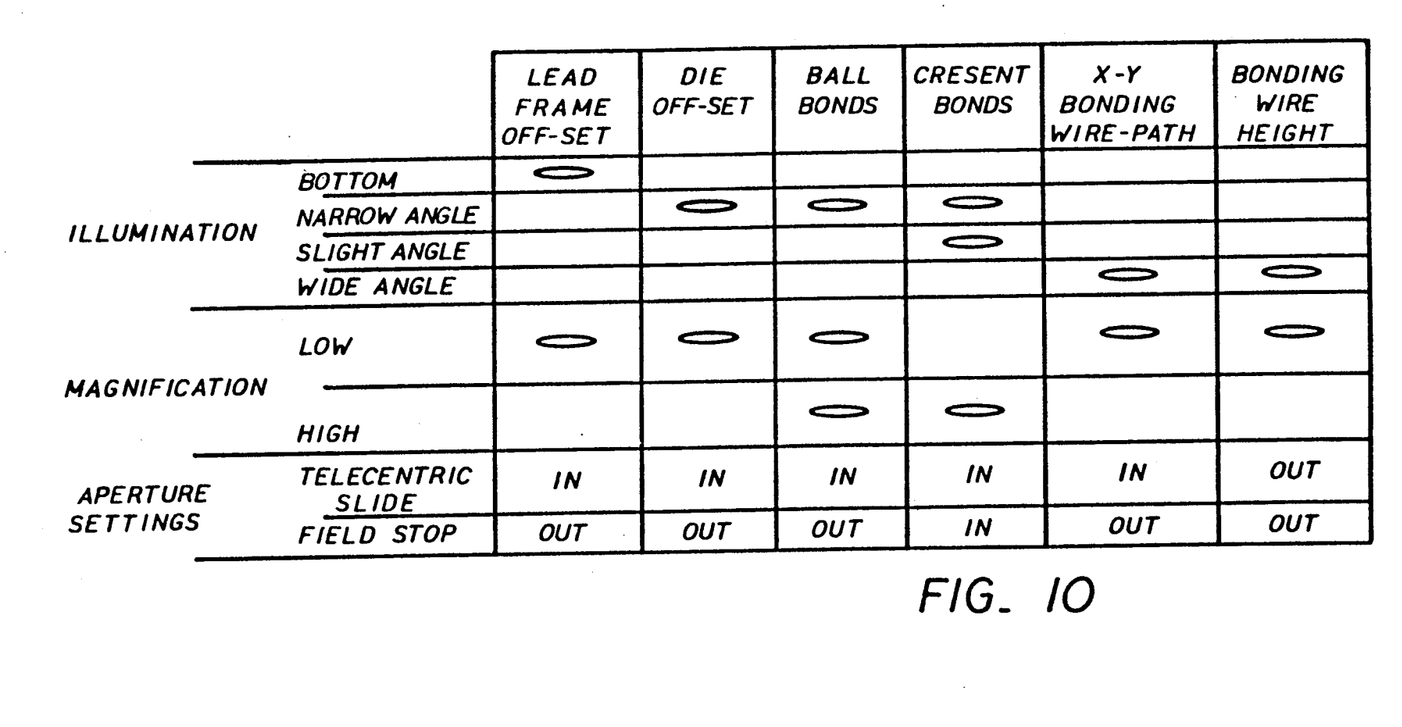
FIG. 10 is a table of the illumination, magnification and aperture setting for various aspects of the inspection process achievable with an optomechanical system in accordance with the preferred embodiment of the present invention.

Much simpler methods, however, may be utilized to determine the best focus, as is shown now with reference to FIG. 9a. The graphic representation of FIG. 9a shows that the point spread function for a point of light imaged by system 12 when in focus reaches a sharp peak and then quickly drops off. As an object goes through focus (as it goes from being out of focus, to in focus, to out of focus), the point spread function corresponding to the intensity of light reflected by this object (or if it does not reflect light, from its surrounding background area which does reflect light) would migrate radially inward and outward. This principle can be illustrated by viewing a point of light in focus and then taking it out of focus. As the point of light moves out of focus, a blurring effect around the periphery of the point of light going out of focus can be detected. Likewise, FIG. 9b illustrates that when system 12 is slightly defocussed, the energy density peak spreads out even more, although the area under the curve remains constant. This implies that the image sensors of the camera, which measure the energy density per unit area, can best detect a maximum energy density when the point light emitter is in perfect focus.

To determine the best focus for inspecting the bonded assembly 10, the system 12 is positioned at a height so that the plane at Z=WD, the maximum point of focus within the depth of focus, does not intersect any bonding wires. Illumination of the bonded assembly 10 is such that a portion of the surface of bonding wire 30 will appear bright and its background (also a portion of the bonded assembly 10) will be generally dark. This assures that the image sensor will mostly see the contribution from a certain point on a bonding wire rather than the surrounding background. As previously described, when a bonding wire is nearing focus, the slope of the intensity curve versus Z-axis relative directional translation is quite sharp while the contribution from the surrounding background, which is out of focus, is small both in energy and in slope.

As the system 12 is moved along the Z-axis toward or away from the bonded assembly 10, the light intensity for any of a number of points along the wire can be captured by computer 16 and stored, together with the known information relating to the height of the system 12 at those points. Thus, system 12 is typically repeatedly moved by a fixed increment in the direction of the bonded assembly 10, and for each new height, the intensity of light collected from the imaged object is compared with the previously recorded values. When the new value of intensity is greater than the old value of intensity, the old value is replaced, together with the value of the height of the system 12 at which the replacement occurred. Hence, successive information regarding the imaged object is discarded and only information relating to the maximum detected height is retained, since the goal is not to attempt to recreate a three-dimensional image of the object, but just to determine its height. Alternatively, a look-up table could be implemented for similarly determining the best focus at every point. Also alternatively, the system could be tuned to determine the height of the object or the best focus where there is a dark object and a light background as previously described.

The above algorithm, which is utilized to determine best focus, may also be utilized to try to isolate an imaged object when the point light source from that object is surrounded by an area of any degree of brightness, provided that the surrounding area is at a different brightness than the object. Because of the radial migration of the point spread function as an object goes through focus, a comparison between intensities at different heights cannot normally be made. However, if slide 130 is positioned "in," the change in magnification as a function of Z-axis directional translation will be only negligible and the intensity at a point light source in the sensor will always correspond to the same point on the bonding wire, which will allow that point light source to be isolated as the intensity of the surrounding area changes. An alternative to using the slide 130 would be to allow for a change in the magnification (rather than holding it constant) while compensating for that change in magnification with the computer 16 through use of standard methods of scan conversion.

Once best focus for the system 12 has been determined, system 12 and computer 16 can be trained to inspect a particular type of bonded assembly. To train the system and store the specifications of the master assembly in the memory of the computer 16, an operator generally operates the system to determine the geometry of a master bonded assembly 10 and the proper placement of ball bonds 32, crescent bonds 34, and bonding wires 30. In addition, the position of system 12 and its height at best focus is also determined for each inspection position and digitally stored in computer 16.

Alternatively, the system may be trained using a computer aided design system to generate the necessary training information, such as the specifications for the position of the die and bonding wires, and the proper size and placement of bonds.

The first operation in inspecting individual bonded assemblies is to determine the alignment of the bonded assembly. Alignment is determined by placing the system 12 at the center of the inspection area, at a predetermined height, and focusing the bonded assembly 10 on the image sensor. The bonded assembly 10 is then illuminated from the bottom by the light source located in support 11. Camera 70 is selected to image the bonded assembly 10 and slide 130 is positioned "in". Light rays passing between the lead frame fingers are imaged into camera 70, converted and stored in computer 16. This stored image is then cross correlated with the same image (or specifications for a computer generated equivalent of an image) of the master assembly stored in the memory of computer 16. The difference between the two images yields an off-set between the position of the training assembly and the bonded assembly which will later be subject to inspection.

The light source within support 11 is then turned off. Illuminator 44 is then utilized to project a narrow angle bright field illumination of die 26. The slide 130 is positioned "in" and low magnification camera 70 is used to determine the off-set between a training die and the die 26 of bonded assembly 10, which is under inspection.

Ball bonds are inspected with the slide 130 positioned "in", narrow angle bright field illumination on, and either the high magnification camera 62 or the low magnification camera 70. The surface of ball bonds 32 appear dark while the surface background appears light. The image of the ball bond 32 is analyzed by computer 16 and the correct size and position of each ball bond is determined.

Crescent bonds 34 are typically inspected with slide 130 positioned "in", narrow angle bright field illumination on, high magnification camera 62, and field stop 56 positioned "in". Fingers 24 and support 11 will appear light, the crescent bond 34 will appear dark, and the bonding wire 30, except for the light center, will be dark. The captured image is analyzed by computer 16. A crescent bond 34 is identified by the large dark area of the image. The bonding wire 30 is identified by its light center and known dimension, and is "cut off" to determine the width, breadth and position of the crescent bond 34.

Because of the irregular shape of lead fingers, narrow angle bright field illumination may result in too few light rays reaching camera 62. In such situations, the slight angle illumination of LED ring 132 should be utilized so that the size of the crescent bond 34 may be accurately determined. Illumination with LED ring 132 may also be required in some situations where the curvature of the surface of the object to be imaged is such that other illumination sources will not reflect light to the imaging camera. Alternatively, some combination of illumination sources can be utilized to achieve the proper optical contrast.

The path of each bonding wire in the X and Y-axis plane, but not in the Z-axis direction, can be determined by positioning slide 130 "in", turning dark field illuminator 92 on, and utilizing camera 62. Bonding wires 30 will appear light and the background will appear dark.

The height of each bonding wire 30 can be determined by positioning slide 130 "out", turning dark field illuminator 92 on, and utilizing camera 70. System 12 is positioned as close to the surface of bonded assembly 10 as is necessary to focus camera 70 on a bonding wire having the greatest sag. The intensities of all points corresponding to locations on the bonding wire 30 are recorded in computer 16. System 12 is then raised by about 50 microns and the intensity of each point corresponding to location on the bonding wire are again recorded. Utilizing previously described methods, the local energy density maximum can be determined from this information to establish the position of best focus, as well as the height of each bonding wire 30.

It should be noted that the present invention is not limited to usage as an optical inspection system. In general, such a system as is described would be useful in automatically locating or referencing any type of object, or measuring the size of a feature of an object in a number of different applications, such as robotics and medical automation fields. The present invention may also be employed to derive a computer aided database from a pre-existing sample of a part to be manufactured.

It should also be noted that the accuracy of Z-axis measurement may be increased by replacing the conventional optical system with a confocal microscope.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. An apparatus for automatically analyzing the physical characteristics of a selected portion of a three dimensional object having specularly reflective surfaces, comprising:
   means for selectively illuminating said portion at one or more angles of incidence of illumination so as to create an optical contrast between said portion and the remainder of said object;
   optical means having an optical axis and operative to collect light reflected from the object and to convert said light into an electrical signal representing an image of said portion; and
   means responsive to said electrical signal and operative to detect maximum contrast between said portion and the remainder of said object and to determine therefrom a set of measurements corresponding to the physical dimensions of said portion from said signal, said set including the position of said portion along said optical axis.

2. An apparatus for automatically analyzing the physical characteristics of a selected portion of a three dimensional object having specularly reflective surfaces, as recited in claim 1, and wherein said means operative to determine includes means for comparing said set of measurements to a predetermined master set of specifications corresponding to acceptable dimensions of a master of said portion to determine if said portion meets said specifications for said portion.

3. An apparatus for automatically analyzing the physical characteristics of a selected portion of a three dimensional object having specularly reflective surfaces as recited in claim 2, wherein said illuminating means includes a narrow angle illumination means for projecting a first column of light incident to said object, said first column being projected at an angle of incidence substantially parallel to the optical axis of said illumination means.

4. An apparatus for automatically analyzing the physical characteristics of a selected portion of a three dimensional object having specularly reflective surfaces as recited in claim 3, wherein said illuminating means further includes a wide angle illumination means for projecting a second column of light incident to said object, said second column's circumference being projected at a large angle of incidence to said optical axis.

5. An apparatus for automatically analyzing the physical characteristics of a selected portion of a three dimensional object having specularly reflective surfaces as recited in claim 4, wherein said illuminating means further includes a slight angle illumination means for projecting a third column of light incident to said object, said third column's circumference being projected at a slight angle of incidence to said optical axis.

6. An apparatus for automatically analyzing the physical characteristics of a selected portion of a three dimensional object having specularly reflective surfaces as recited in claim 5, wherein said means includes:
   a photo-responsive device for collecting said light and creating said electrical signal; and
   optical system for directing and focusing said light incident to said photo-responsive device.

7. An apparatus for automatically analyzing the physical characteristics of a selected portion of a three dimensional object having specularly reflective surfaces as recited in claim 5, wherein said optical system includes means for selectively varying the numeric aperture of said lens system.

8. An apparatus for automatically analyzing the physical characteristics of a selected portion of a three dimensional object having specularly reflective surfaces as recited in claim 7, wherein said varying means includes a first numeric aperture control means for selectively increasing or reducing the numeric aperture of said optical system without affecting said first, second, or third column s circumference.

9. An apparatus for automatically analyzing the physical characteristics of a selected portion of a three dimensional object having specularly reflective surfaces as recited in claim 4, wherein said collecting means includes:
   a photo-responsive device for collecting said light and creating said electrical signal; and
   an optical system for directing and focusing said light incident to said photo-responsive device.

10. An apparatus for automatically analyzing the physical characteristics of a selected portion of a three dimensional object having specularly reflective surfaces as recited in claim 9, wherein said optical system includes means for selectively varying the numeric aperture of said optical system.

11. An apparatus for automatically analyzing the physical characteristics of a selected portion of a three dimensional object having specularly reflective surfaces as recited in claim 10, wherein said varying means includes a first numeric aperture control means for selectively increasing or reducing the numeric aperture of said optical system without affecting the circumference of said first or second column.

12. An apparatus for automatically analyzing the physical characteristics of a selected portion of a three dimensional object having specularly reflective surfaces as recited in claim 3, wherein said collecting means is operative to output said signal, and wherein said comparing means includes a computer for receiving said signal, determining said set of measurements from said signal, comparing said set of measurements to said master set of specifications stored in the memory of said computer, determining if said portion meets said master set of specifications, and developing and outputting a control signal for controlling the operation of said illuminating means and said collecting means.

13. An apparatus for automatically analyzing the physical characteristics of a selected portion of a three dimensional object having specularly reflective surfaces as recited in claim 12, wherein said illuminating means includes variable aperture means through which said first column is projected and means for selectively varying said aperture.

14. An apparatus for automatically analyzing the physical characteristics of a selected portion of a three dimensional object having specularly reflective surfaces as recited in claim 13, wherein said variable aperture includes
   a movable first aperture stop for selectively increasing or reducing the aperture through which said first column is projected; and wherein said varying means includes
   a first stop control means responsive to said control signal and operative to position said first aperture stop in and out of coaxial alignment with said optical axis.

15. An apparatus for automatically analyzing the physical characteristics of a selected portion of a three dimensional object having specularly reflective surfaces as recited in claim 2, wherein said collecting means is operative to output said signal, and wherein said comparing means includes a computer for receiving said signal, determining said set of measurements from said signal, comparing said set of measurements to a predetermined master set of specifications stored in the memory of said computer and corresponding to the physical dimensions of a master image of said portion, determining if said portion meets said master set of specifications, and developing and outputting a control signal for controlling the operation of said illuminating means and said collecting means.

16. An apparatus for automatically analyzing the physical characteristics of a selected portion of a three dimensional object having specularly reflective surfaces as recited in claim 15, wherein said illuminating means includes:
   a lens having a first aperture coaxial with said optical axis;
   an aperture slide having a second aperture smaller than said first aperture and operative to be positioned in and out of coaxial alignment with said optical axis; and
   a slide control means responsive to said control signal and operative to change the position of said slide.

17. An apparatus for automatically analyzing the physical characteristics of a selected portion of a three dimensional object having specularly reflective surfaces as recited in claim 16, wherein said illumination means includes:
   a narrow angle illumination means for projecting a first column of light incident to said object, said first column's circumference being projected at an angle of incidence substantially parallel to the optical axis of said illumination means;
   a wide angle illumination means for projecting a second column of light incident to said object, said second column's circumference being projected at a large angle of incidence to said optical axis; and
   a slight angle illumination means for projecting a third column of light incident to said object, said third column's circumference being projected at a slight angle of incidence to said optical axis.

18. An apparatus for automatically analyzing the physical characteristics of a selected portion of a three dimensional object having specularly reflective surfaces as recited in claim 17, wherein said slight angle illumination means includes a ring of selectively actuable light sources disposed around the perimeter of said first aperture.

19. An apparatus for automatically analyzing the physical characteristics of a selected portion of a three dimensional object having specularly reflective surfaces as recited in claim 18, wherein said wide angle illumination means includes:
   a wide angle illumination support disposed on the object said of said lens, said support having a third aperture formed therein and operative to encircle said portion; and
   a ring of selectively actuable light sources disposed around the perimeter of said third aperture.

20. An apparatus for automatically analyzing the physical characteristics of a selected portion of a three dimensional object having specularly reflective surfaces as recited in claim 16, and further including:
   a first drive means responsive to said control signal and operative to control the position of said apparatus; and
   a second drive means responsive to said control signal and operative to control the position of said object with respect to said apparatus.

21. A method for automatically determining the distance from a selected portion of a three dimensional object to an optical analysis system imaging said portion as a means of measuring a physical relationship of said portion to said object, comprising the steps of:
   positioning said system with respect to said objects in a manner so as to cause the optical depth of field for said system to be above or below said portion;
   moving said system relative to said object in a manner so as to cause said portion to go through being in focus by said system;
   collecting light reflected from said object and determining the height of said system and the intensity of light reflected from said portion for each of a number of positions of said system; and
   selecting a position at which said system detected a maximum contrast of reflected light between said portion and said portion's background as the distance from said portion to said portion.

22. A method for automatically determining the distance from a selected portion of a three dimensional object to an optical inspection system as recited in claim 21, wherein said maximum contrast of reflected light is created by selectively illuminating said object in such a manner so as to maximize the contrast between said portion and said portion's background.

23. A method for automatically determining the distance from a selected portion of a three dimensional object to an optical inspection system as recited in claim 22, and further including the step of illuminating said object with a first column of light in a manner so as to create said maximum contrast of reflected light between said portion and said portion's background.

24. A method for automatically determining the distance from a selected portion of a three dimensional object to an optical inspection system as recited in claim 23, wherein said step of illuminating said object includes the step of determining an angle of incidence for said first column's circumference which will cause said portion to reflect light toward said system and said portion's background to reflect light way from said system.

25. A method for automatically determining the distance from a selected portion of a three dimensional object to an optical inspection system as recited in claim 24, wherein said angle of incidence is substantially parallel to the optical axis of said system.

26. A method for automatically determining the distance from a selected portion of a three dimensional object to an optical inspection system as recited in claim 24, wherein said angle of incidence is at a slight angle to the optical axis of said system.

27. A method for automatically determining the distance from a selected portion of a three dimensional object to an optical inspection system as recited in claim 24, wherein said angle of incidence is at a large angle to the optical axis of said system.

28. A method for automatically analyzing the physical characteristics of selected portions of a three dimensional object having specularly reflective surfaces, comprising the steps of: p1 (a) illuminating a portion of said object to be analyzed at one or more angles of incidence of illumination so as to create an optical contrast between said portion and the remainder of said object;

(b) collecting light reflected from said portion and the remainder of said object and converting said light into an electrical signal representing an image of said object;

(c) determining a set of measurements corresponding to the physical dimensions of said portion from said signal, said set including the elevation of said portion relative to the remainder of said object;

(d) comparing said set of measurements to a predetermined master set of specifications derived from acceptable dimensions of a master for said portions and said object to determine if said portion meets said specifications for said portion; and (e) repeating steps (a) through (d) for each portion of said object to be inspected.

29. A method for automatically analyzing the physical characteristics of selected portions of a three dimensional object having specularly reflective surfaces as recited in claim 28, and further including the steps of:

(f) preceding step (a), establishing a first off-set between the position of said object and the corresponding position of said master for said object; and (g) following step (c), adjusting said set of measurements by said first off-set to compensate for changes in position between said object and said master for said object.

30. A method for automatically analyzing the physical characteristics of selected portions of a three dimensional object having specularly reflective surfaces as recited in claim 29, wherein said step of collecting light includes the step of transmitting light reflected from said object through an optical system and onto a photo-responsive device operative to collect said light and convert said light into said electrical signal.

31. A method for automatically analyzing the physical characteristics of selected portions of a three dimensional object having specularly reflective surfaces as recited in claim 30, wherein said step of transmitting light includes the step of varying the numeric aperture of said optical system in a manner so as to restrict the surface area of said photo-responsive device exposed to said light.

* * * * *